(12) United States Patent
Tucker

(10) Patent No.: US 6,871,477 B1
(45) Date of Patent: Mar. 29, 2005

(54) METHOD OF MANUFACTURING TRANSDERMAL PATCHES

(75) Inventor: Mark Rupert Tucker, Chipping Norton (GB)

(73) Assignee: United Pharmaceutical Manufacturing Co. Limited, Amman (JO)

( * ) Notice: Subject to any disclaimer, the term of this patent is extended or adjusted under 35 U.S.C. 154(b) by 0 days.

(21) Appl. No.: 09/673,221

(22) PCT Filed: Apr. 14, 1999

(86) PCT No.: PCT/GB99/01138

§ 371 (c)(1),
(2), (4) Date: Oct. 6, 2000

(87) PCT Pub. No.: WO99/52513

PCT Pub. Date: Oct. 21, 1999

(30) Foreign Application Priority Data

Apr. 14, 1998 (GB) ............................................ 9807917

(51) Int. Cl.[7] ............................................. B65B 31/00
(52) U.S. Cl. ........................... 53/433; 53/560; 53/433; 53/434; 53/451; 53/551; 53/201
(58) Field of Search ........................ 53/560, 433, 434, 53/451, 551, 201

(56) References Cited

U.S. PATENT DOCUMENTS

| | | | | |
|---|---|---|---|---|
| 3,210,908 A | * | 10/1965 | Samberg | 53/546 |
| 4,004,399 A | | 1/1977 | Borrello | 53/180 |
| 4,306,656 A | * | 12/1981 | Dahlem | 206/390 |
| 4,614,076 A | | 9/1986 | Rathemacher | 53/433 |
| 4,769,974 A | * | 9/1988 | Davis | 53/433 |
| 4,782,647 A | * | 11/1988 | Williams et al. | 53/454 |
| 4,845,926 A | | 7/1989 | Davis | 53/451 |
| 5,268,179 A | * | 12/1993 | Rudella | 424/449 |
| 5,268,209 A | * | 12/1993 | Hunt et al. | 428/34.3 |
| 5,656,285 A | * | 8/1997 | Sablotsky et al. | 424/448 |
| 5,938,032 A | * | 8/1999 | Svec et al. | 206/532 |
| 5,962,011 A | * | 10/1999 | DeVillez et al. | 424/448 |
| 6,261,405 B1 | * | 7/2001 | Laprade | 156/324 |
| 6,315,854 B1 | * | 11/2001 | Anhauser et al. | 156/267 |

FOREIGN PATENT DOCUMENTS

WO    WO 96/10398    4/1996    ............ A61K/9/70

* cited by examiner

Primary Examiner—Scott A. Smith
Assistant Examiner—Brian Nash
(74) Attorney, Agent, or Firm—Stites & Harbison PLLC; Marvin Petry

(57) ABSTRACT

A continuous process for forming a transdermal patch which comprises the steps of: continuously feeding a strip of material comprising a layer of permeable membrane; continuously feeding into close proximity and in face-to-face relationship with the first strip a second strip formed of impermeable backing material; passing the first and second strips together through a filling and sealing station in which the material containing an active substance is introduced between the strips and pouches are formed by first sealing devices which seal the strips together in a longitudinal direction of the strips and second sealing devices which seal the strips together in a transverse direction of the strips; the size of the pouches being adjusted by adjusting the number position and/or frequency of operation of the first sealing devices and/or by adjusting the number position and/or frequency of operation of the second sealing devices.

18 Claims, 1 Drawing Sheet

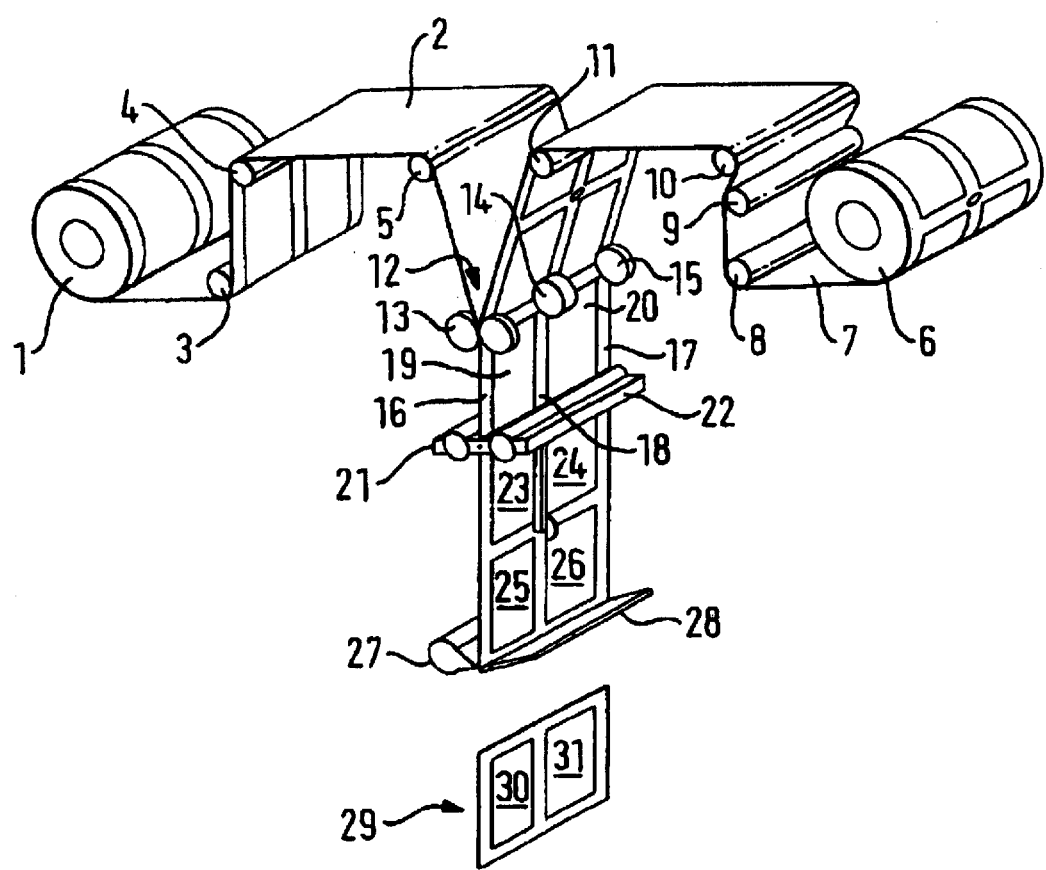

METHOD OF MANUFACTURING TRANSDERMAL PATCHES

CROSS REFERENCE TO RELATED APPLICATIONS

The present application being filed herewith claims priority under 35 U.S.C. § 371 and 119 to Patent Cooperation Treaty (PCT) patent application PCT/GB99/01138, filed Apr. 14, 1999, which in turns claims priority to British Patent Application number 9807917.1, filed in the United Kingdom on Apr. 14, 1998.

This invention relates to a method of manufacturing transdermal patches, for example the so-called nicotine patches which can be applied to the skin of a person who wishes to receive some nicotine whilst giving up smoking.

One particularly satisfactory form of patch is disclosed in United Kingdom Patent Specification No. 2232892, where it is broadly defined as an occlusive body for the transdermal administration of a physiologically active substance, the body comprising an impermeable backing and a microporous or permeable membrane which define a cavity therebetween, said physiologically active substance being contained within said cavity in liquid form, said microporous or permeable membrane being permeable to and in contact with said physiologically active substance and the liquid material confined between said impermeable backing and said microporous or permeable membrane within said cavity being substantially immobilised by a viscous flowable gel, characterised in that either;

a) said membrane is hydrophilic and the contents of said cavity are hydrophobic, or b) said membrane is hydrophobic and said cavity contains a hydrophilic wetting agent;

whereby, in use, passage of said physiologically active substance through said microporous membrane is rate-controlling and said physiologically active substance is released from said microporous membrane at a rate that is substantially constant over a period of hours.

Typically the occlusive body in the form of the patch has, in going from one side to the other, several layers which may include: (i) a disposable, removable protective layer, (ii) a layer of adhesive, (iii) the permeable membrane or membranes, (iv) a layer of gel containing the physiologically active substance (such as nicotine), and (v) the layer of an impermeable backing material.

In practice the first three (or more) layers may be employed as a pre-formed laminate. It is then necessary to apply the active substance (layer (iv)) to the laminate (to the combination of layers (i) to (iii)) and then to secure the active substance in place by providing the backing layer (layer (v)).

Typically when manufacturing a product of this nature, the materials are fed horizontally and a discrete amount of the active substance is deposited at a fixed interval, or station, along the laminate, with the backing material than being brought into position in order to cover the active substance prior to the backing material being secured, for example by sealing, to the laminate in regions around the discrete amounts of active substance. The process is non-continuous and known as 'form, fill, seal' such as is demonstrated by a blister packer. It requires substantial re-tooling if volumetric changes to the reservoir are desired.

Bearing in mind that the active substance is normally present in a gel, it can be appreciated that there are considerable handling problems associated with providing the appropriate amounts of the gel at neatly spaced intervals along the laminate without the gel being exposed to the environment. Moreover, when it is wished to vary the volume of the gel, so as to vary the amount of active substance in the patch, or to vary the skin contact area of the product, (assuming that the concentration of active substance in the gel remains the same), it can be difficult to alter the machine whilst in operation so that the desired effect is achieved.

Equipment already exists for wrapping items such as so-called telephone cards, which are cards for insertion into a telephone machine to allow the user to use the telephone for the duration of the unused units electromagnetically held in the telephone card. In such equipment a first layer of material is caused to travel vertically downwards close to, and parallel to, a second layer of material. Often one layer is transparent and the other is opaque and contains instructions and other information. The two layers of material are brought together and are sealed to each other by opposing pairs of sealing devices, e.g. heated wheels, which act on the opposing longitudinal edges of the two strips of material being brought together. In addition, an intermittent sealing mechanism acts transversely across the juxtaposed layers already joined at their opposing longitudinal edge regions, so that a pouch results. As the pouch is being formed a telephone card, or the like, is fed into the pouch which still remains open along its upper (fourth) edge. Once the card or other item is correctly located in the pouch, and while both layers continue to move-downwardly, the fourth open edge of the pouch is closed, typically by the same horizontal sealing mechanism. In fact, the most efficient way of achieving this is for the upper edge of a lower pouch to be sealed at the same time as the lower edge of the immediately upper pouch is being sealed. Both sealing operations can be carried out simultaneously by the same sealing arrangement.

If desired at about the same time as the sealing is being effected to form the last transverse seal, or immediately downstream thereof or at a much later stage, the pouches can be separated from each other by cutting, or else a line of weakness can be formed in the region between the upper seal of the lower pouch and the lower seal of the upper pouch so that the pouches are still joined in end to end relationship but with a line of weakness which can readily be ruptured.

Somewhat similar equipment can also be used for creating pouches containing other products, such as sugar or sauces (for use in restaurants).

According to a first aspect of the present invention, there is provided a method of forming a transdermal patch, which comprises the steps of:

feeding at a first linear speed a strip of materials comprising a disposable layer, a layer of adhesive and a layer of a permeable membrane;

feeding into close proximity and in face-to-face relationship with the first strip at least one second strip formed of impermeable backing material (s), at the same first linear speed;

passing the first and second strips together through a first sealing station at which at least the opposed longitudinal edge regions of the strips are secured together, optionally with intermediate regions of the strips being secured along their lengths, so as to form at least one elongate chamber;

passing the first and second strips joined at least at their longitudinal edges, through a second sealing station at which the strips are sealed to each other transversely at intervals along the strips, whereby the or each chamber becomes an open-topped pouch;

introducing a liquid containing an active substance into the pouch or pouches, once formed; and sealing the pouches along their previously open edges so as to form completely sealed pouches.

According to a second aspect of the present invention there is provided a continuous process for forming a transdermal patch which comprises the stops of:

continuously feeding a strip of material comprising a layer of permeable membrane;

continuously feeding into close proximity and in face-to-face relationship with the first strip a second strip comprising an impermeable backing material;

passing the first and second strips together through one or more filling and sealing stations in which the material containing an active substance is introduced between the strips and pouches are formed by first sealing devices which seal the strips together in a longitudinal direction of the strips and second sealing devices which seal the strips together in a transverse direction of the strips;

The size of the pouches being adjusted by adjusting the number position and/or frequency of operation of the first sealing devices and/or by adjusting the number position and/or frequency of operation of the second sealing devices.

The process is continuous as a result of the dosing and patch formation happening in a synchronised/simultaneous manner. This is distinct from the blister technique which is a station-by-station function and non-continuous.

Conveniently, at the second sealing station the upper previously open region of a pouch or pouches is sealed and the sealing simultaneously closes the bottom of the pouch or pouches immediately above the first mentioned pouch or pouches.

The method can also include a separation cutting step, in which a transverse cutting exercise takes place so as to separate one sealed pouch containing the active substance from the adjacent pouches upstream and downstream.

If a tear-tab at one corner of the patch is required, a suitable "kiss-cut" function can be provided at this stage. For example, a die can be used to cut through the disposable layer, allowing the disposable layer to be peeled away from the layer of adhesive at the "kiss-cut". In addition, other functions such as registration, embossing and de-bossing, can be performed at, or immediately after, this stage.

In addition, when the two strips are first brought together and sealed along their longitudinal edges and when there is one or more additional longitudinal seal being created intermediate the edge region seals, then there will be two or more pouches being created, and it is desirable to separate those laterally adjacent pouches at a suitable downstream station. This can be achieved by, for example, rollers acting on opposite sides of the joined strips with at least one of the rollers having a cutting edge so as to separate laterally adjacent pouches.

Preferably, when effecting the method of the present invention, a gas flushing system is employed, which can be achieved by placing a small bore tube adjacent the liquid (gel) delivery tube, which ensures that the pouch will, when sealed, effectively only contain the gel itself and the flushing gas, for example nitrogen. Alternatively, instead of employing an inert flushing gas, the filling and sealing can be effected in a "vacuum".

The sealing of the adjacent strips can be effected by opposing pairs of sealing devices (e.g. heated rollers), and the means by which the liquid (gel) containing the active substance is introduced can take the form of a tube the lower, open end of which can be at a level considerably below the axes of rotation of those sealing devices, and can be positioned at a level just above where the transverse sealers are employed which come together intermittently to provide the transverse seals across the strips at the desired spaced intervals. It will be appreciated that careful synchronisation of the different pieces of quipment which carry out the sealing and cutting steps is required, but existing technology is readily available for this.

When it is desired to increase the active amount of substance, whilst retaining the concentration of the active substance constant in the gel, it is clearly necessary to provide a larger volume of the gel. In order to accommodate the larger volume, the pouch needs to be larger and this can be achieved in one or more ways. If, for instance, during pouch production three pouches are being produced side by side, it is possible to reduce the number of pouches to two which will increase the available width of each pouch. This is done by removing one of the pairs of sealing devices (e.g. heating rollers) and adjusting the location of the remaining intermediate pair of sealing devices; moreover, one of the dosing nozzles is removed.

Alternatively, or in addition, the timing of the transverse sealing is adjusted to take place at longer intervals with the result that longer pouches are formed.

Obviously when the transverse sealing is less frequent during the formation of the longer pouches, it is also necessary that there is corresponding adjustment to the transverse cutting equipment so that the cutting remains along the seal which separates one sealed pouch or row of pouches from the adjacent pouch or row of pouches.

It is to be appreciated that, even when the volume of the pouch is being altered, it is possible to continue to feed in the first and second strips at the same linear feed speed. Furthermore, the two or more in-feed rolls of material do not need to be changed as part of the retooling exercise common in other manufacturing methods. In other words, the same materials and some rolls can be used without adjustment to obtain a different pouch size. In fact, it is a great advantage of the present invention that variation in the volume of the pouch desired does not necessitate any alteration to the components responsible for feeding in the two starting strips of material. The handling of such strips is a delicate matter and it is therefore of considerable advantage to maintain the feed speeds at a constant. This is because continuous processes exert a constant pressure/strain on the materials resulting in less damage and/or distortion of the final product and a "flatter" more aesthetically pleasing pouch than intermittent ones. Indeed, intermittent or non-continuous processes such as blister packers have a stop-start motion that can cause damage by stretching the material.

It is a relatively simple matter, through the let appropriate control equipment, to cause the transverse sealing components to operate at longer or shorter intervals so as to produce longer or shorter pouches, and equally it is relatively simple for the same control equipment to coordinate the components responsible for the transverse cutting without re-tooling the machine.

It has been found by experiment that the process according to the present invention can be used to manufacture pouches as small as 2 $cm^2$. This contrasts with the prior art processes in which a minimum pouch size of no less than 5 $cm^2$ was possible.

The tube or tubes, or like, responsible for injecting the gel containing the active substance into the pouches remains in the same position and injects the appropriate volume of gel into the pouch as the transverse seal is being formed or immediately after it has been formed. Accurate dosing equipment is available to ensure that precisely the desired amount of gel is deposited into each pouch and can be adjusted to compensate for an increase, or decrease, in the volumetric requirements of the pouch in a similar way to the timing adjustment of the sealing devices.

Preferably, the materials are fed through the stations in a substantially vertical direction and the liquid containing an active ingredient is introduced into the pouch or pouches in a substantially vertical direction. However, alternatively the materials may be fed through the stations in a substantially horizontal direction whilst the liquid is still introduced in a substantially vertical direction.

For a better understanding of the present invention, and to show how the same may be carried into effect, reference will now be made, by way of example, to the accompanying drawing, which shows a perspective view of a method in accordance with the present invention being conducted on equipment having the appropriate facilities to effect the method.

In the drawing there are shown a roll 1 of backing material in the form of a strip 2 which is drawn off from the roll 1 and passed around a tensioning roller 3, then over a guide roller 4 and another guide roller 5 and passed further downstream. Somewhat similarly, but starting from the opposite side of the equipment, there is a roll 6 of multi-layer material (of the type mentioned above) with the strip 7 of that material (e.g. in the form of a laminate) being drawn off from the roll 6 and passed around its own tensioning roller 8 and then around three guide rollers 9, 10 and 11 and downstream into the region of a "nip" 12 where it meets the strip 2. The two strips 2 and 7 pass between three pairs of sealing devices in the form of pairs of heated rollers 13, 14 and 15 which have the effect of sealing the strips 2 and 7 at their longitudinally opposing edge regions 16 and 17 and also at a central location 18, so that the region between the two strips 2 and 7 is divided into two pouches 19 and 20 which are open at their upper and lower ends. However, as those pouches 19 and 20 travel downwardly they encounter the transverse intermittent sealing system which comprises two heated bars 21 and 22 which are generally separated from each other but intermittently are brought together to form a horizontal seal across the downwardly travelling strips 2 and 7 whereby the pouches 19 and 20 are then sealed along their lower edges, as well as their vertical edges. Not shown (for the sake of clarity) are two tubes which project into the pouches 19 and 20 with the lower end regions of the tubes being just above the heated bars 21 and 22. Adjacent those two tubes are two smaller tubes (also not shown) through which an inert gas (particularly nitrogen) under pressure is introduced into the pouches 19 and 20 to create an inert atmosphere during the dosing of the pouches by the introduction of discrete doses of gel through the main tubes into the pouches 19 and 20. When the heated bars 21 and 22 are separated the filled pouches 19 and 20 can move further downward to the position occupied by thee pouches 23 and 24. It can readily be seen that the heating and sealing action of the bars 21 and 22 simultaneously seals the lower edges of the pouches 19 and 20 and the upper edges of the pouches 23 and 24. It is also to be appreciated that the strips 2 and 7 when separate and when travelling together move at the same linear speed throughout in a continuous manner. For this reason the bars 21 and 22, when acting on the strips 2 and 7, move at the same speed as those strips so that the smooth progress of those strips is not impaired.

Shown below the pouches 23 and 24 are two further pouches 25 and 26 produced immediately before the production of the pouches 23 and 24. As shown in the drawing, the lower edge of the pouches 25 and 26 is being acted on by cutting devices 27 and 28 which cut transversely across the combined strips 2 and 7 to separate the pair of pouches 25 and 26 from the pair 29 shown below as pouches 30 and 31.

It can readily be appreciated that comprehensive equipment, such as a bandolier mechanism, can be employed to draw off the strips 2 and 7 at a uniform speed and to feed them into the sealing system consisting of the heated rollers 13, 14 and 15 at the same speed and to pass the united strips 2 and 7 through the sealing system 21, 22 and through the cutting system 27, 28 at the same uniform speed.

If longer pouches are required, it is merely on necessary to cause the sealing system 21, 22 to operate for the same duration but at greater intervals and for the cutting system 21, 28 also to operate at correspondingly greater intervals. It will also readily be appreciated that the provision of the three pairs 13, 14 and 15 of heated rollers of the sealing system causes the production of two pouches 19 and 20, and that by increasing or decreasing the number of pairs of heated rollers or other sealing devices there is a corresponding increase or decrease in the number of pouches generated in side-by-side relationship.

The dosing through the tubes (not shown) of the gel containing the active substance (e.g. nicotine) can be effected by sophisticated dosing equipment which is available on the market, for example from the company Hibar Systems Limited.

Although the dosing of the gel through the tube or tubes into the pouch or pouches is effected as intermittent deposits, the supply of the inert gas through the adjacent tube or tubes to create an inert atmosphere in the pouch or pouches being formed can be effected continuously.

With suitable control equipment it will be possible, at the touch of a button, to alter the location of the heated rollers 13, 14 and 15 thereby varying the width of the pouches and also to alter the frequency of the sealing operation of the heating components 21, 22 and cutting components 27, 28 so as to vary the length of the pouches. No re-tooling is necessary. Thus variation in the magnitude of the pouches can be effected without having to replace any of the components of the equipment by replacement components. All that needs to be varied is the location of the heated rollers 13, 14 and 15 and/or the frequency of operation of the transverse sealing system, 21, 22 and the cutting system 27, 28. If desired, the backing material can be flesh-coloured or clear on that side which is to face outwards When the patch is applied to a person. At further stages downstream, the individual pouches can be cropped to provide a 'kiss-cut' 'tear-tab' and be separately packed in their own individual wrappers and batches of the wrappers collected together in packets or other suitable containers.

What is claimed is:

1. A continuous process for forming a transdermal patch holding an active substance, said process comprising the steps of:

continuously feeding at a linear speed a first strip of materials comprising a disposable layer, a layer of adhesive and a layer of a permeable membrane permeable to the active substance;

continuously feeding in close proximity and in face-to-face relationship with the first strip at least one second strip formed of impermeable backing material(s), at the same linear speed;

passing the first and second strips together through a first sealing station at which at least the opposed longitudinal edge regions of the strips are secured together;

passing the first and second strips joined at least at their longitudinal edges, through a second sealing station at which the strips are sealed to each other transversely at intervals along the strips, whereby the or each chamber becomes an open-topped pouch;

introducing an accurate predetermined dosage of a liquid or gel containing an active substance into the pouch or pouches, once formed, in synchronous with the linear speed; and sealing the pouches along their previously open edges so as to form completely sealed pouches thereby forming the transdermal patch.

2. A continuous process as claimed in claim 1, in which, at the second sealing station the previously open region of a pouch or pouches is sealed and the sealing simultaneously closes the adjacent region of the pouch or pouches immediately upstream of the first mentioned pouch or pouches.

3. A continuous process as claimed in claim 1, further including a separation cutting step in which a transverse cutting exercise takes place so as to separate one sealed pouch containing the active substance from the adjacent pouches upstream and downstream.

4. A continuous process as claimed in claim 3, wherein the separation cutting step comprises separating one sealed pouch from the adjacent pouches along a tear-tab.

5. A continuous process as claimed in claim 1, in which the two strips are first brought together and sealed along their longitudinal edges and separately or simultaneously one or more additional longitudinal seals are created intermediate the edge region seals thereby creating two or more laterally adjacent pouches across the width of the strips.

6. A continuous process as claimed in claim 5, in which the laterally adjacent pouches are separated in a longitudinal cutting step in which rollers, at least one of which has a cutting edge, act on opposite sides of the join strips, so as to separate the laterally adjacent pouches.

7. A continuous process as claimed in claim 1, further comprising a gas flushing step in which the or each pouch is flushed with gas during the step in which liquid or gel is introduced.

8. A continuous process as claimed in claim 7, in which in the gas flushing step, a small bore tube is placed adjacent a filling tube and flushing gas is ejected from the small bore tube directly into the pouch.

9. A continuous process as claimed in claim 1, in which the filling and sealing steps are effected at a pressure lower than atmospheric pressure.

10. A continuous process as claimed in claim 1, in which the sealing of adjacent strips is effected by opposing pairs of longitudinal or transverse sealing devices.

11. A continuous process as claimed in claim 10, in which the means by which the liquid or gel containing the active substance is introduced takes the form of a filling tube which is inserted into the or each pouch.

12. A continuous process as claimed in claim 11, in which the lower end of the filling tube is at a level considerably below the axis of rotation of the sealing devices.

13. A continuous process as claimed in claim 11, in which the filling tube is positioned at a level just above where the transverse sealing devices are disposed.

14. A continuous process as claimed in claim 10, in which the filling tube is positioned at a level just above where the transverse sealing devices are disposed.

15. A continuous process as claimed in claim 10, further comprising the step of adjusting the number of pouches being produced side by side, by adding or removing one or more pairs of longitudinal sealing devices and adjusting the location of the intermediate sealing devices.

16. A continuous process as claimed in claim 10, further comprising the step of adjusting the size of the pouches, by adjusting the timing of transverse sealing devices, thereby changing the length of the pouches.

17. A continuous process as claimed in claim 1, in which the strips are fed in a substantially vertical direction and the liquid or gel containing an active ingredient is introduced into the pouch or pouches in a substantially vertical direction.

18. A continuous process as claimed in claim 1 wherein the intermediate regions of the strips are secured along their lengths so as to form at least one elongated chamber.

* * * * *